(12) United States Patent
Mabuchi et al.

(10) Patent No.: US 11,014,053 B2
(45) Date of Patent: May 25, 2021

(54) CELLULOSE ACETATE-BASED ASYMMETRIC HOLLOW FIBER MEMBRANE

(71) Applicant: TOYOBO CO., LTD., Osaka (JP)

(72) Inventors: Kimihiro Mabuchi, Osaka (JP); Haruhiko Kohyama, Osaka (JP); Yoshinori Takii, Otsu (JP)

(73) Assignee: TOYOBO CO., LTD., Osaka (JP)

( * ) Notice: Subject to any disclaimer, the term of this patent is extended or adjusted under 35 U.S.C. 154(b) by 0 days.

(21) Appl. No.: 16/344,153

(22) PCT Filed: Oct. 31, 2017

(86) PCT No.: PCT/JP2017/039247
§ 371 (c)(1),
(2) Date: Apr. 23, 2019

(87) PCT Pub. No.: WO2018/079807
PCT Pub. Date: May 3, 2018

(65) Prior Publication Data
US 2020/0070099 A1    Mar. 5, 2020

(30) Foreign Application Priority Data
Oct. 31, 2016   (JP) .............................. JP2016-212836

(51) Int. Cl.
*B01D 69/08*   (2006.01)
*B01D 63/02*   (2006.01)
(Continued)

(52) U.S. Cl.
CPC ............. *B01D 69/08* (2013.01); *B01D 63/02* (2013.01); *B01D 69/02* (2013.01); *B01D 71/16* (2013.01);
(Continued)

(58) Field of Classification Search
CPC ...... B01D 69/02; B01D 69/08; B01D 69/087; B01D 63/02; B01D 71/16;
(Continued)

(56) References Cited

U.S. PATENT DOCUMENTS 5,643,452 A   7/1997  Althin et al.
5,736,046 A   4/1998  Althin et al.
(Continued)

FOREIGN PATENT DOCUMENTS

CN        1049108 A     2/1991
CN      101472671 A     7/2009
(Continued)

OTHER PUBLICATIONS

International Search Report dated Jan. 30, 2018, issued in counterpart application No. PCT/JP2017/039247 (1 page).
(Continued)

*Primary Examiner* — John Kim
(74) *Attorney, Agent, or Firm* — Westerman, Hattori, Daniels & Adrian, LLP

(57) ABSTRACT

A hollow fiber membrane including a dense layer at least on an inner surface side of the hollow fiber membrane, in which when the inner surface of the hollow fiber membrane is observed under an atomic force microscope, a plurality of groove-like recesses oriented in a lengthwise direction of the hollow fiber membrane are observed, an aspect ratio defined as a ratio of a length to a width of each of the recesses is greater than or equal to 3 and less than or equal to 30, a yield strength of the hollow fiber membrane in a dry state is greater than or equal to 30 g/filament, and a breaking elongation is less than or equal to 20%/filament.

4 Claims, 3 Drawing Sheets

(51) Int. Cl.
   *B01D 69/02* (2006.01)
   *B01D 71/16* (2006.01)

(52) U.S. Cl.
   CPC .... *B01D 2325/023* (2013.01); *B01D 2325/24* (2013.01)

(58) Field of Classification Search
   CPC ......... B01D 2325/023; B01D 2325/06; A61M 1/3413; D01F 1/08; D01F 2/28
   See application file for complete search history.

(56) References Cited

U.S. PATENT DOCUMENTS

| | | | |
|---|---|---|---|
| 6,372,136 B1 * | 4/2002 | Nakatsuka | B01D 69/02 210/500.23 |
| 2009/0178969 A1 | 7/2009 | Hanakawa et al. | |
| 2011/0114559 A1 | 5/2011 | Fislage et al. | |
| 2018/0065093 A1 | 3/2018 | Takada et al. | |

FOREIGN PATENT DOCUMENTS

| CN | 101703893 A | 5/2010 |
|---|---|---|
| CN | 101883624 A | 11/2010 |
| CN | 102448508 A | 5/2012 |
| DE | 69320000 T2 | 4/1999 |
| EP | 1 029 584 A1 | 8/2000 |
| EP | 3 278 867 A1 | 2/2018 |
| JP | 6-55047 A | 3/1994 |
| JP | 2009-95515 A | 5/2009 |
| JP | 2011-78920 A | 4/2011 |
| JP | 2011-212638 A | 10/2011 |
| NO | 30/05006 A1 | 5/1990 |
| NO | 2010/147763 A2 | 12/2010 |
| WO | 2016/159333 A1 | 10/2016 |

OTHER PUBLICATIONS

Extended Search Report dated May 27, 2020, issued in counterpart EP Application No. 17865100.6 (7 pages).
Extended Search Report dated May 27, 2020, issued in counterpart EP Application No. 17865663.3 (7 pages).
Final Office Action dated Sep. 24, 2020, issued in U.S. Appl. No. 16/344,984 (19 pages).
Office Action dated Jun. 15, 2020, issued in U.S. Appl. No. 16/344,984 (10 pages).
Office Action dated Dec. 2, 2020, issued in counterpart IN Application No. 201917021292, with English Translation. (5 pages).
Office Action dated Jan. 22, 2021, issued in counterpart CN Application No. 201780067442.X, with English Translation. (14 pages).
Office Action dated Mar. 1, 2021, issued in CN Application No. 201780067440.0, with English Translation. (counterpart to U.S. Appl. No. 16/344,984) (16 pages).
Pang, Xinlu (Editor), "Modern Nephrology Theory and Application", Published by Hebei Science & Technology Press, Shijiazuang, Jun. 30, 2013, p. 433, with English Translation.; Cited in CN Office Action dated Mar. 1, 2021. (5 pages).
Notice of Allowance dated Feb. 24, 2021, issued in U.S Appl. No. 16/344,984 (2 pages).

* cited by examiner

CELLULOSE ACETATE-BASED ASYMMETRIC HOLLOW FIBER MEMBRANE

TECHNICAL FIELD

The present invention relates to a hollow fiber membrane made of a cellulose acetate-based polymer. The present invention more specifically relates to a hollow fiber membrane containing a cellulose acetate-based polymer and having an asymmetric structure suitable for a blood purification application, in particular, hemodiafiltration.

BACKGROUND ART

Blood purification includes methods such as hemodialysis, hemofiltration, and hemodiafiltration. The hemodialysis is a method for bringing blood into contact with a dialysis fluid with a semi-permeable membrane interposed therebetween to remove a waste product accumulated in a body by means of a diffusion phenomenon. Purified blood is returned to the body again. Normally, the treatment is conducted three times per week, and it takes about four hours per treatment. On the other hand, the hemofiltration is a method for ultra-filtering a large amount of blood to remove a waste product as well as a body fluid. Since a large amount of body fluid is removed, a supplemental fluid (12 to 20 L/time) is required to be supplied. It is said that, although the hemofiltration is superior to the hemodialysis in removal of a medium to high-molecular-weight waste product, the hemofiltration is inferior to the hemodialysis in removal of a low-molecular-weight waste product. Under such circumstances, in recent years, the hemodiafiltration attracts attention since, by combining the hemodialysis with the hemofiltration, the hemodiafiltration enables a wide range of waste products ranging from the low-molecular-weight waste products to the high-molecular-weight waste products to be removed efficiently, and the present applicant has filed related applications (PTL 1 and 2). These patent literatures disclose a hollow fiber membrane applicable to hemodiafiltration and the like. In this hollow fiber membrane, by improving uniformity and smoothness of a membrane surface, adsorption and clogging of blood protein and the like can be restricted even at the time of large-quantity filtration.

CITATION LIST

Patent Literature

PTL 1: Japanese Patent Laying-Open No. 2009-95515
PTL 2: Japanese Patent Laying-Open No. 2011-78920

SUMMARY OF INVENTION

Technical Problem

The hemodiafiltration therapy includes predilution hemodiafiltration therapy for infusing the fluid into the blood before the blood enters a dialyzer and postdilution hemodiafiltration therapy for infusing the fluid into the blood before the blood exits from the dialyzer. In the predilution hemodiafiltration therapy, since the blood is diluted before entering the dialyzer, the concentration of substances to be removed in the blood is lowered. Although the removing efficiency is lowered due to the diffusion, the predilution hemodiafiltration therapy is advantageous in that protein clogging to the dialyzer is hard to occur, and in that temporal performance degradation is hard to occur. On the other hand, in the postdilution hemodiafiltration therapy, since the hemoconcentration in the dialyzer is significant, problems occur such as an increase in albumin leakage as compared to the predilution hemodiafiltration therapy, and a frequent occurrence of protein clogging to the dialyzer. In general, in the postdilution hemodiafiltration therapy, the required amount of the replacement fluid is about ⅓ of that in the predilution hemodiafiltration therapy to exert an equivalent effect to that in the predilution hemodiafiltration therapy. Thus, further improvement of a hollow fiber membrane is required for adsorption of a smaller amount of protein and restriction of clogging to apply the hollow fiber membrane to the postdilution hemodiafiltration therapy.

An object of the present invention is to provide a hollow fiber membrane that can achieve stable performance suitable for postdilution hemodiafiltration therapy by optimizing a structure of a dense layer on an inner surface of the hollow fiber membrane and to restrict temporal adsorption and clogging of protein.

Solution to Problem

The present invention has the following configuration.
(1) A hollow fiber membrane comprising a dense layer at least on an inner surface side of the hollow fiber membrane, wherein when the inner surface of the hollow fiber membrane is observed under an atomic force microscope, a plurality of groove-like recesses oriented in a lengthwise direction of the hollow fiber membrane are observed, an aspect ratio defined as a ratio of a length to a width of each of the recesses is greater than or equal to 3 and less than or equal to 30, a yield strength of the hollow fiber membrane in a dry state is greater than or equal to 30 g/filament, and a breaking elongation is less than or equal to 20%/filament.
(2) The hollow fiber membrane according to (1), wherein the hollow fiber membrane includes the dense layer and a support layer, and the support layer has a pore larger than a pore in the dense layer.
(3) The hollow fiber membrane according to (1) or (2), wherein the hollow fiber membrane is mainly made of a cellulose acetate-based polymer.
(4) A hollow fiber membrane module comprising the hollow fiber membrane according to any one of (1) to (3).

Advantageous Effects of Invention

By optimizing a structure of a dense layer on an inner surface of a hollow fiber membrane, it is possible to provide a hollow fiber membrane that can restrict adsorption and clogging of protein and the like even in a case of increases in blood flow rate and/or filtration rate and that is applicable not only to predilution hemodiafiltration therapy but also to postdilution hemodiafiltration therapy.

DESCRIPTION OF EMBODIMENTS

Figure 1:
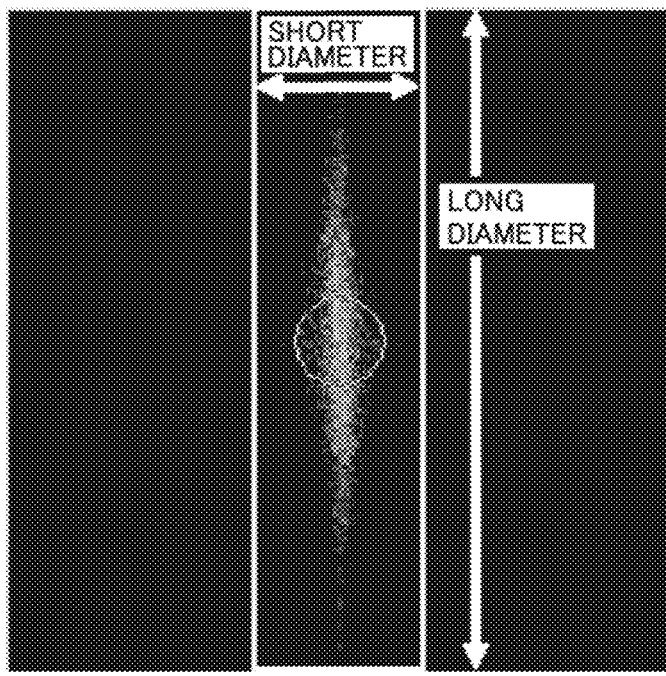
FIG. 1 illustrates an example of an image obtained by Fourier-transforming data of a recess on an inner surface of a hollow fiber membrane observed under an atomic force microscope.

A hollow fiber membrane according to the present invention is in a category of an ultrafiltration membrane. Specifically, an average pore diameter of fine pores of the membrane is approximately 3 nm to 50 nm. The membrane has as large fine pores as to prevent a high-molecular-weight substance having a several thousand to several hundred thousand molecular weight and a colloidal substance from being permeated therethrough and to allow a medium-molecular-weight substance having a molecular weight less than or equal to that of the high-molecular-weight substance and ions to permeate therethrough.

Conventionally, for blood compatibility and performance improvement, development has been advanced toward enhancement of smoothness of an inner surface of the hollow fiber membrane in order to restrict adsorption and clogging of a blood cell component and plasma protein to the surface of the membrane. However, the conventional development intention has a limitation in responding to increases in blood flow rate and filtration rate. The present inventors have finally arrived at the present invention upon discovering that, by providing a hollow fiber membrane including a dense layer at least on an inner surface side thereof, in which when the inner surface thereof is observed under an atomic force microscope, a plurality of groove-like recesses oriented in a lengthwise direction of the hollow fiber membrane are observed, an aspect ratio defined as a ratio of a length to a width of each of the recesses is greater than or equal to 3 and less than or equal to 30, a yield strength of the hollow fiber membrane in a dry state is greater than or equal to 30 g/filament, and a breaking elongation is less than or equal to 25%/filament, adsorption and clogging of a blood cell component, protein, and the like to the surface of the membrane can be restricted even in a case where the hollow fiber membrane is used in blood purification therapy under a severe condition for the hollow fiber membrane such as postdilution hemodiafiltration therapy.

In the present invention, as a material for the hollow fiber membrane, a cellulose acetate-based polymer is preferably used. As the cellulose acetate-based polymer, cellulose diacetate and cellulose triacetate, having some hydroxyl groups capped, are preferable from the viewpoint of restriction of complement activation and blood compatibility such as low blood coagulation. In a case where a hollow fiber membrane mainly including a cellulose-based polymer is used for blood purification, white blood cells may transiently decrease, and this is problematic in terms of blood compatibility. However, using the cellulose acetate-based polymer, having some of the hydroxyl groups of the cellulose substituted with acetyl groups, is advantageous in improvement in blood compatibility. Specifically, relatively-low-viscosity cellulose triacetate having a degree of acetylation of 53 to 62 and a 6% viscosity of more than 140 mPa·s and less than 200 mPa·s is preferable.

Figure 5:
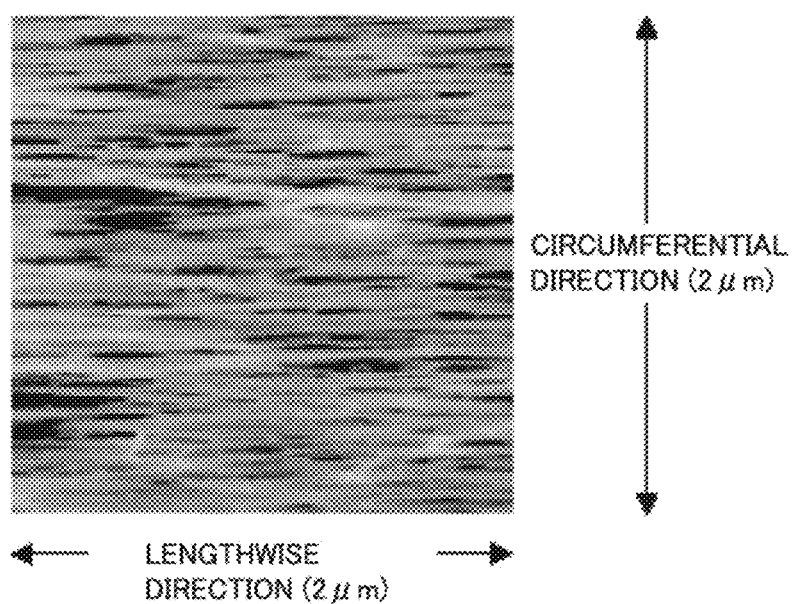
FIG. 5 illustrates a surface shape image when the inner surface of the hollow fiber membrane is observed under the atomic force microscope.

In the present invention, when the inner surface of the hollow fiber membrane is observed using an atomic force microscope under below-mentioned conditions, the surface preferably includes a plurality of groove-like recesses oriented in a lengthwise direction of the hollow fiber membrane (FIG. 5). More specifically, in an about 2 μm-square observation range, the surface preferably includes ten or more groove-like recesses oriented in the lengthwise direction of the hollow fiber membrane. Although the detailed reason is unknown, not only the adsorption of protein and the like is decreased but also the transient decrease of white blood cells tends to be restricted. The reason for this may be that, when the distance between the recesses is within a predetermined range, a blood rectifying effect is enhanced. For this reason, fifteen or more recesses are preferably observed on the inner surface.

In the present invention, an average length (long diameter) of the recesses is preferably greater than or equal to 200 nm and less than or equal to 500 nm. In a case where the length of the recess is too short, a blood cell component, protein, and the like easily accumulate in the recess. The reason for this may be that the blood rectifying effect is lowered. Thus, the effect of the present invention is hard to be obtained. Also, in a case where the length of the recess is too long, this may cause a defect in the membrane surface structure such as breakage of the recess. Here, the average length (long diameter) is an average value of five values including a highest value and a lowest value as described below.

In the present invention, an average width (short diameter) of the recesses is preferably greater than or equal to 10 nm and less than or equal to 100 nm. In a case where the width of the recess is too short, a sufficient blood flow rectifying effect may not be obtained. In a case where the width of the recess is too long (short), a blood cell component and protein easily accumulate in the recess, and the effect of the present invention is hard to be obtained. Here, the average width (short diameter) is an average value of five values including a highest value and a lowest value as described below.

In the present invention, an aspect ratio (average length/average width) defined as a ratio of the average length to the average width of the recesses is preferably greater than or equal to 3 and less than or equal to 30. In a case where the aspect ratio is too low, the recess is in a shape of having a long width for the length. Thus, the blood flow rectifying effect is hard to be obtained, and a blood cell component easily accumulates in the recess. Conversely, a too high aspect ratio probably causes no problem.

In the present invention, an average depth of the recesses is preferably less than or equal to 30 nm. In a case where the depth of the recess is too long, stagnation may easily occur in flow of the fluid such as blood, permeability of β2-microglobulin and the like may be lowered, and temporal stability of permeability may be lowered, although these negative effects depend on the width of the recess. Also, the transient decrease of white blood cells may be enhanced. Also, the average depth of the recesses is preferably greater than or equal to 10 nm. In a case where the depth of the recess is too short, the rectifying effect on flow of the fluid such as blood cannot be obtained, and temporal stability of permeability may be lowered. For this reason, the average depth of the recesses is preferably greater than or equal to 10 nm.

In the present invention, the hollow fiber membrane preferably includes a dense layer on an inner surface side thereof and preferably includes at a part other than the dense layer a pore enlarged as much as to cease to be permeation resistance to the substances. Specifically, the hollow fiber membrane includes the dense layer on the inner surface thereof and a structure causing a pore to be gradually enlarged toward an outer surface thereof or a structure causing a pore to be enlarged from the inner surface to the outer surface in the beginning, to be in an approximately equal size from a middle portion to a portion close to the outer surface, and to be enlarged or shrunk around the outer surface.

Figure 3:
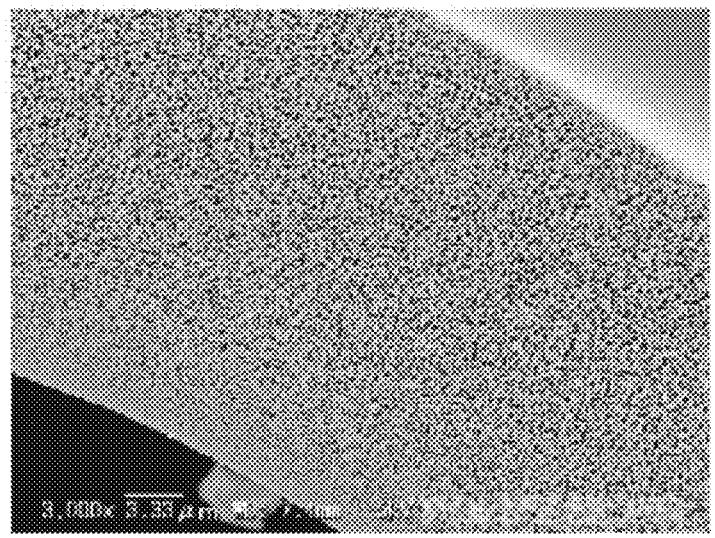
FIG. 3 illustrates an example of an image of a cross-section of the hollow fiber membrane observed at 3,000 magnification with use of a scanning electron microscope.

In the present invention, the dense layer is a portion having no void recognized substantially in a photo (FIG. 3) obtained by capturing an image of the cross-section of the hollow fiber membrane at 3,000 magnification with use of a scanning electron microscope (SEM). Note that "substantially" means that the polymer portion and the void portion are not visually distinguished clearly on a photo having a normal photo size (L photo size). A thickness of the dense layer is preferably less than or equal to 2.5 µm, and more preferably less than or equal to 2 µm. In a case where a fluid to be treated (blood) is supplied to a hollow portion of the hollow fiber membrane and is subject to a treatment, the dense layer is preferably thinner from the viewpoint of lowering the permeation resistance to the substances. However, the too thin layer may cause a defect in the inner surface structure to impair the integrity of the dense layer. Thus, the thickness of the dense layer is preferably greater than or equal to 0.01 µm, and more preferably greater than or equal to 0.1 µm. Also, a support layer portion other than the dense layer may have a fine pore diameter or include a void having as large a diameter as to cease to be permeation resistance to the substances and may have as large a thickness as to enable the membrane shape to be maintained.

In the present invention, to secure flow stability of blood, an inside diameter of the hollow fiber membrane is preferably greater than or equal to 130 µm and less than 280 µm. In a case where the inside diameter of the hollow fiber membrane is too short, the linear velocity of flowing blood may be too high, and a blood cell component may be damaged when the blood flow rate is increased. Conversely, in a case where the inside diameter of the hollow fiber membrane is too long, the size of a module (blood purifier) needs to be increased to fit into the area of the membrane, and use convenience will thus be impaired.

In the present invention, a membrane thickness of the hollow fiber membrane is preferably greater than or equal to 18 µm and less than 30 µm although the membrane thickness is not particularly limited. In a case where the membrane thickness of the hollow fiber membrane is too small, permeability is enhanced, but it is difficult to maintain required strength. Also, in a case where the membrane thickness of the hollow fiber membrane is too large, permeation resistance to the substances is raised, and permeability of the substances to be removed is insufficient in some cases.

To obtain the hollow fiber membrane according to the present invention, the hollow fiber membrane is preferably formed by means of dry-wet spinning. As a spinning dope, a cellulose acetate-based polymer mixed and dissolved with a solvent and a non-solvent as needed is used. As a core solution, a coagulable solution to the cellulose acetate-based polymer is used. The spinning dope is discharged from a circular portion (slit portion) of a double-tube nozzle, at the same time, the core solution is discharged from a central hole (inner hole), and the fluid passes through an areal traveling portion and is then introduced into a coagulation bath to coagulate the shape of the hollow fiber membrane. The obtained hollow fiber membrane is washed to remove excessive solvent and the like, a membrane pore hold-back agent is impregnated into the hollow portion and the fine pore (or the void) as needed, and the hollow fiber membrane is dried and rolled up.

A technical means for obtaining the hollow fiber membrane according to the present invention will be described in detail below. To control the structure of the inner surface of the hollow fiber membrane, it is important to strictly control a process of bringing the core solution into contact with the spinning dope (dope) to form the membrane surface. That is, optimization of a discharge linear velocity ratio (linear velocity ratio) between the spinning dope and the core solution and a draft ratio is important. Specifically, in a state of using as the core solution a coagulable solution to the spinning dope containing the cellulose acetate-based polymer, it is important to set the discharge linear velocity of the spinning dope and the discharge linear velocity of the core solution to be approximately equal to each other. Here, "to be approximately equal" means to set the ratio between the discharge linear velocity of the spinning dope and the discharge linear velocity of the core solution to 0.95 to 1.05.

In the present invention, the discharge linear velocity of the spinning dope is a value obtained from the cross-sectional area of the circular portion (slit portion) and the discharge amount of the spinning dope, and the discharge linear velocity of the core solution is a value obtained from the cross-sectional area with reference to the inside diameter of the circular portion (slit portion) and the discharge amount of the core solution. For example, in a case of discharging the spinning dope at a rate of 3 cc/min. and discharging the core solution at a rate of 2 cc/min. with use of a double-tube nozzle having a slit outside diameter of 500 µm and having a slit inside diameter of 300 µm, the linear velocity ratio (discharge linear velocity of spinning dope/discharge linear velocity of core solution) is obtained in the following manner.

> Discharge linear velocity of spinning dope (m/min.)=discharge amount of spinning dope/cross-sectional area of slit portion=3 cc/1.26× $10^{-3}$ cm$^2$/100=23.8

> Discharge linear velocity of core solution (m/min.)=discharge amount of core solution/cross-sectional area with reference to inside diameter of slit portion=2 cc/7.07×$10^{-4}$ cm$^2$/100=28.3

> Linear velocity ratio=discharge linear velocity of spinning dope/discharge linear velocity of core solution=23.8/28.3=0.84

In a case where the ratio (linear velocity ratio) between the discharge linear velocity of the spinning dope and the discharge linear velocity of the core solution is too high or too low, the velocity difference between the spinning dope and the core solution is significant. Hence, turbulence of flow at the interface occurs, and the surface structure of the membrane tends to be coarse (markedly uneven). Such a phenomenon easily occurs especially in a case where the discharge linear velocity of the core solution is relatively high.

Also, in the present invention, the draft ratio represents drawing velocity from coagulation bath/discharge linear velocity of spinning dope. In order to control the structure of the inner surface of the hollow fiber membrane in the scope of the present invention, the draft ratio is preferably set to 0.80 to 0.85. For example, in a case where the drawing velocity from the coagulation bath is 50 m/min., and where the discharge linear velocity of the spinning dope is 40 m/min., the draft ratio is 1.25. When the draft ratio is high, the hollow fiber membrane whose structure is being coagulated is excessively extended. As a result, the recess formed on the inner surface is extended, and in an extreme case, a defect such as breakage of the recess occurs. Also, when the draft ratio is low, an effect of uniforming fine projections and recesses (wrinkles) generated in a lengthwise direction of the hollow fiber membrane cannot be exerted, and the rectifying effect of the fluid flowing near the inner surface of the hollow fiber membrane may not be obtained.

By employing the aforementioned conditions, the characteristic structure of the hollow fiber membrane according to the present invention can be achieved. Hereinbelow, other manufacturing preconditions for employing the aforementioned conditions will be described.

In the present invention, as the spinning dope, a cellulose acetate-based polymer mixed and dissolved with a solvent and a non-solvent is preferably used. Specifically, the spinning dope is preferably prepared with a ratio of cellulose acetate-based polymer/solvent/non-solvent=15 to 20/52 to 64/16 to 33.

In the present invention, as the solvent for the cellulose acetate-based polymer, N-methylpyrrolidone (hereinbelow abbreviated as NMP in some cases), dimethylformamide, dimethylacetamide, dimethylsulfoxide, or the like is preferably used. Also, examples of the non-solvent include ethylene glycol, triethylene glycol (hereinbelow abbreviated as TEG in some cases), polyethylene glycol, glycerol, propylene glycol, and alcohols. These solvents and non-solvents have favorable compatibility with water.

In the present invention, as the core solution, an aqueous solution containing a solvent, a non-solvent, and water can be used. The core solution is preferably prepared with a ratio of solvent/non-solvent/water=0 to 14/0 to 6/80 to 100, is more preferably a mixed solution of a non-solvent and water, and is further preferably water itself. Here, examples of the water include ion-exchange water, distilled water, RO water, purified water, and ultrapure water.

The obtained spinning dope and core solution are respectively discharged from the slit portion and the central hole of the double-tube nozzle at the same time, pass through the areal traveling portion, and are then dipped into the coagulation bath to be formed in a hollow fiber shape. To obtain the hollow fiber membrane having an inside diameter of approximately 200 μm, the nozzle having a slit outside diameter of 250 to 300 μm and a slit inside diameter of 180 to 230 μm is preferably used. Also, as for the nozzle temperature, the temperature on the spinning dope side is preferably adjusted to 55 to 65° C. as a heating medium temperature, and the temperature on the core solution side is preferably adjusted to 10 to 15° C. as a cooling medium temperature.

The length of the areal traveling portion is preferably 5 mm to 100 mm depending on the spinning velocity. Also, the humidity and temperature of the areal traveling portion may be controlled as needed. After the fluid passes through the areal traveling portion, the fluid is dipped into the coagulation bath prepared with a ratio of solvent/non-solvent/water=49 to 56/21 to 24/20 to 30 to form the hollow fiber membrane. Since asymmetry of the membrane cross-section is raised as the water content of the coagulation liquid is lower, a ratio of solvent/non-solvent/water=52.5 to 56/22.5 to 24/20 to 25 is more preferable. Also, the temperature of the coagulation bath is preferably adjusted to 40 to 50° C.

The hollow fiber membrane drawn from the coagulation bath is then washed with water to remove excessive solvent and non-solvent and is dipped into a glycerol bath as needed to replace water in the hollow fiber membrane with an aqueous glycerol solution. At this time, the concentration of the glycerol is preferably 85 to 93% by weight. Also, the temperature of the aqueous glycerol solution is preferably adjusted to 88 to 96° C.

The hollow fiber membrane drawn from the glycerol bath is dried and rolled up. The drying temperature is preferably adjusted to 35 to 60° C.

A predetermined number of the obtained hollow fiber membranes provided with crimps as needed are housed in a case to produce a module including entrance and exit of blood and entrance and exit of a dialysis fluid.

In the present invention, a yield strength of the hollow fiber membrane in a dry state is preferably greater than or equal to 30 g/filament, and a breaking elongation is preferably less than or equal to 20%/filament. The yield strength is preferably higher since the higher yield strength leads to a high yield ratio of manufacture of the blood purifier (module). However, in a case where the breaking elongation is too high, the following problems occur. The yield ratio of manufacture of the module is rather lowered, the performance may change due to heat history during storage and transport, and filtration stability is lowered (ATMP is increased) although the reason is unknown. Also, in a case where the breaking elongation is too low, the hollow fiber membrane is hard to be handled. Hence, the breaking elongation is preferably greater than or equal to 10%/filament, and more preferably greater than or equal to 15%/filament. In the present invention, not only by setting strength and elongation in a predetermined range but also by optimizing the structure of the inner surface, the hollow fiber membrane excellent in balance between performance and handling can be obtained.

Since it is assumed that the hollow fiber membrane according to the present invention is used not only for hemodialysis but also under severe conditions such as hemodiafiltration and hemofiltration, the hollow fiber membrane according to the present invention has the following characteristics in addition to basic performance: water permeability (UFR) of pure water measured at 37° C. is greater than or equal to 200 ml/(m$^2$·hr·mmHg) and less than or equal to 1500 ml/(m$^2$·hr·mmHg), clearance (membrane area with reference to inside diameter: 2.1 m$^2$) of (β2-MG (β2-microglobulin) measured at a filtration flow velocity of 15 ml/min. with use of bovine plasma is greater than or equal to 65 ml/min. and less than or equal to 90 ml/min., and an amount of leakage of useful protein such as albumin is less than or equal to 1.5 g/(3 L removal, membrane area with reference to inside diameter: 2.1 m$^2$).

In other words, fouling such as adsorption of protein in the dense layer on the inner surface of the membrane can be restricted, and high-level filtration stability can be maintained even after hemoconcentration resulting from filtration advances. Accordingly, the hollow fiber membrane is expected to exert stable and high performance in postdilution hemodiafiltration therapy.

In the present invention, in a below-mentioned filtration stability test, when a blood test liquid is fed to an inner side (hollow portion) of the hollow fiber membrane of the blood purifier (module) at a rate of 350 mL/min., and the blood is filtered at a rate of 75 mL/min., a difference between TMP after 15 minutes of start of feeding and TMP after 240 minutes is preferably less than or equal to 13 mmHg. The difference is more preferably less than or equal to 10 mmHg.

Also, in the present invention, when a below-mentioned protein adsorption amount test is conducted, the amount is preferably less than or equal to 5.0 mg/m$^2$. The amount is more preferably less than or equal to 4.5 mg/m$^2$, and further preferably less than or equal to 4.0 mg/m$^2$.

EXAMPLES

Hereinbelow, the present invention will be described more specifically by way of examples, but the present invention is not limited to these examples.

(Measurement of Outside Diameter, Inside Diameter, and Thickness of Hollow Fiber Membrane)

The outside diameter, inside diameter, and thickness of a hollow fiber membrane are obtained by inserting an appropriate number of hollow fiber membranes into a hole of ϕ3 mm opened at the center of a glass slide so as not to fall, cutting the membranes along the upper and lower surfaces of the glass slide with use of a blade to obtain hollow fiber membrane cross-section samples, and measuring the short diameter and the long diameter of the hollow fiber membrane cross-section with use of a projector, Nikon-V-12A. The short diameters and long diameters of each hollow fiber membrane cross-section in two directions were measured, and respective arithmetic average values were regarded as the inside diameter and outside diameter of the hollow fiber membrane cross-section. The thickness was calculated by (outside diameter−inside diameter)/2. Similar measurement was conducted for five cross-sections including a maximum cross-section and a minimum cross-section, and respective average values were regarded as the inside diameter, the outside diameter, and the thickness.

(Calculation of Membrane Area)

A membrane area A (m$^2$) of a module was obtained with reference to the inside diameter of the hollow fiber membrane.

$$A = n \times \pi \times d \times L$$

In this equation, n is the number of the hollow fiber membranes in the dialyzer, π is pi, d is an inside diameter of the hollow fiber membrane (m), and L is an effective length of the hollow fiber membrane in the dialyzer (m).

(6% Viscosity)

61.67 g of a mixed solvent [methylene chloride:methanol=91:9 (ratio by weight)] was collected in a conical flask and was charged with 3.00 g of a sample dried for two hours at 105±5° C., and the flask was tightly closed. The solution was thereafter shaken in a horizontal shaker for 1.5 hours and was further shaken in a rotary shaker for 1 hour for complete dissolution. Subsequently, the temperature of the obtained 6 wt/vol % solution was adjusted to 25±1° C. in a constant temperature oven, downflow time between mark lines for timekeeping was measured with use of an Ostwald viscometer, and the viscosity was obtained from the following equation.

6% viscosity (mPa·s)=downflow time (sec)/viscometer coefficient Meanwhile, the viscometer coefficient was obtained from the following equation by measuring downflow time (sec) in a similar procedure to the above with use of a standard solution for viscometer calibration.

Viscometer coefficient=[standard solution absolute viscosity (mPa·s)×solution density (1.235 g/cm$^3$)]/[standard solution density (g/cm$^3$)×standard solution downflow time (sec)]

(Measurement of Breaking Strength and Elongation and Yield Strength and Elongation)

Figure 4:
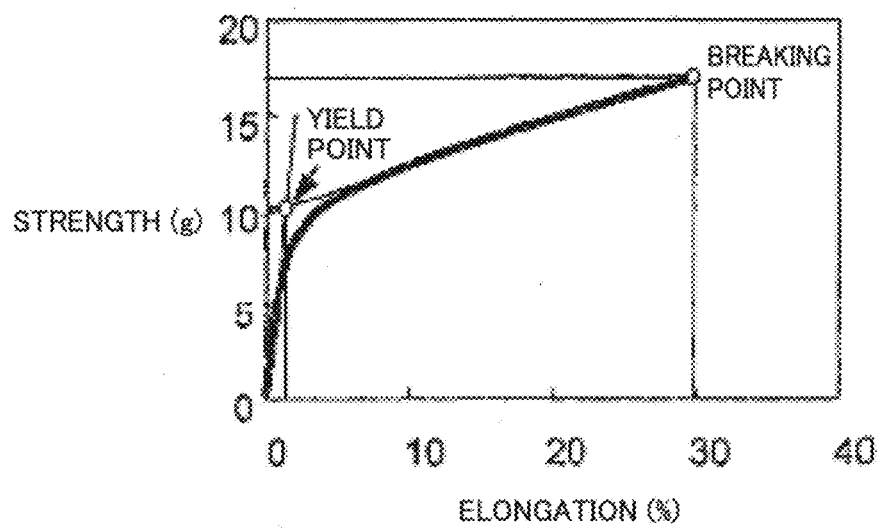
FIG. 4 illustrates an example of a measurement result of strength and elongation of one dried hollow fiber membrane.

The strength and elongation of the hollow fiber membrane were measured with use of a Tensilon universal tester (UTMII manufactured by Toyo Baldwin). One dried hollow fiber membrane was cut to have a length of approximately 15 cm, was attached between chucks (distance: approximately 10 cm) without flexure, and was pulled at a crosshead speed of 10 cm/min. under a temperature condition of 20±5° C. and a humidity condition of 60±10% RH. The breaking elongation and the breaking strength were read from the obtained chart. Also, as illustrated in FIG. 4, auxiliary lines were provided from the S-S curve, and a cross point of the two auxiliary lines was defined as a yield point. Strength at the point was regarded as the yield strength, and elongation at the point was regarded as the yield elongation.

(Measurement of Protein Adsorption Amount)

A module having a membrane area, with reference to the inside diameter of the hollow fiber membrane, of 1.5 m$^2$ was used. Liquid paraffin was enclosed on the dialysis fluid side in advance to prevent the aqueous solution from flowing into the blood side from the dialysis fluid side. 500 ml of an aqueous albumin solution at 37° C. adjusted to have a concentration of 100 mg/l was prepared and was circulated in the blood side of the module heated at 37° C. in advance for four hours at a flow velocity of 200 ml/min. The adsorption amount was obtained with use of the following equation based on an initial concentration and a concentration after circulation of the aqueous albumin solution. Meanwhile, the albumin concentration was obtained by means of a bromcresol green method (BCG method) with use of A/G B-Test Wako (manufactured by Wako Pure Chemical Industries, Ltd.).

Adsorption amount (mg)=(initial concentration−concentration after circulation)×0.5

(Filtration Stability Evaluation)

Bovine blood at 37° C. added with citric acid to restrict coagulation was used. The bovine blood was diluted with bovine plasma to adjust hematocrit to 30%. The blood was fed to the inner side of the hollow fiber membrane of the blood purifier (module) at a rate of 350 mL/min. and was filtered at a rate of 75 mL/min. At that time, the filtrate was returned to the blood for circulation. The blood purifier was sufficiently replaced with saline in advance for the purpose of preventing hemolysis. After 15 minutes of start of circulation, it was confirmed by collecting the filtrate in a measuring cylinder that a predetermined filtration flow rate was obtained. At the same time, pressure at a blood entrance (Pi), a blood exit (Po), and a filtrate ejecting portion (Pf) was measured in a pressure chamber portion of the dialysis circuit, and TMP was calculated by the following equation.

$$TMP=Pf-(Pi+Po)/2$$

In a similar manner, TMP after 240 minutes was measured, and αTMP was calculated by the following equation.

$$\alpha TMP=|TMP240-TMP15|$$

(Measurement of Hollow Fiber Membrane Inner Surface Structure)

Figure 2:
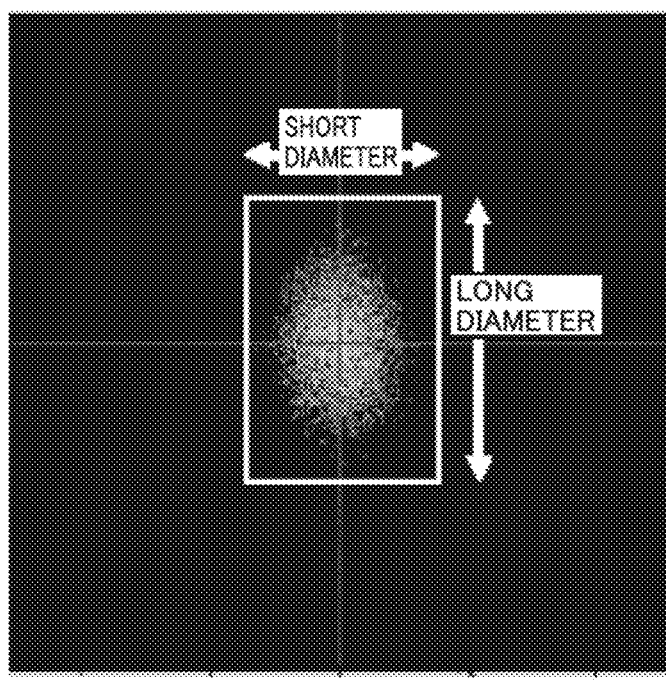
FIG. 2 illustrates another example of an image obtained by Fourier-transforming data of a recess on the inner surface of the hollow fiber membrane observed under the atomic force microscope.

The hollow fiber membrane for evaluation was used as a sample by exposing the inner surface thereof. The structure was observed with use of an atomic force microscope (AFM), E-Sweep/SPI4000 (Hitachi High-Tech Science Corporation). The observation mode was a DFM mode, the scanner was a 20 μm scanner, the cantilever was DF-3, and the observation range was 2 μm square. Planarization processing was conducted with use of attached software (SPI-Win Version 4.17F7). Also, an FFT image was produced from a planarized AFM image with use of the same software. The planarization processing optimal to the observation image needs to be conducted by conducting two-dimensional tilt correction and Y-direction flat processing. The obtained FFT image was converted into a jpeg image, and the jpeg image was subject to an image analysis with use of image analysis measuring software WinROOF2013 (Mitani Corporation). The taken image was subject to binarization (color coordinate system: RGB, R: threshold value 0 to 170, G: threshold value 0 to 170, B: threshold value 0 to 170). Based on the obtained image, the long diameter of the recess and the short diameter of the recess were automatically measured to calculate the aspect ratio (FIGS. 1 and 2). Five values including a highest value and a lowest value were measured for each of the long and short diameters to obtain the average long diameter and the average short diameter.

Aspect ratio=average long diameter of recesses/average short diameter of recesses (Observation of Hollow Fiber Membrane Structure)

The hollow fiber membrane was washed lightly to remove attached glycerol. The wet hollow fiber membrane was quickly dipped into liquid nitrogen, frozen, and then taken out of the liquid nitrogen. The hollow fiber membrane was bent and cut in the frozen state to obtain a sample for cross-section observation. The obtained sample was fixed on a sample stage for carbon vapor deposition. The deposited sample was observed with use of a scanning electron microscope (S-2500 manufactured by Hitachi, Ltd.) at an acceleration voltage of 5 kV and at 3,000 magnification.

Example 1

17.3% by mass of cellulose triacetate (6% viscosity=162 mPa·s, Daicel Chemical Industries, Ltd.), 57.89% by mass of NMP (Mitsubishi Chemical Corporation), and 24.81% by mass of TEG (Mitsui Chemicals, Inc.) were uniformly dissolved to prepare a spinning dope. The obtained spinning dope was discharged from a slit portion of a double-tube nozzle at a rate of 1.80 cc/min., and at the same time, RO water serving as a core solution was discharged from a central hole at a rate of 2.18 cc/min. The double-tube nozzle having a slit outside diameter of 270 μm and having a slit inside diameter of 200 μm was used. The temperature of a heating medium on the spinning dope side was set to 65° C., and the temperature of a cooling medium on the core solution side was set to 10° C. The spinning dope discharged from the nozzle passed through a 25 mm areal traveling portion, was then introduced into a coagulation liquid having a temperature of 43° C. and having a ratio of NMP/TEG/water=54.6/23.4/22, and was coagulated. The coagulated hollow fiber membrane was drawn at a velocity of 57.0 m/min., washed with water, dipped into glycerol, dried, and rolled up. Meanwhile, in the water washing process and the glycerol dipping process, care was taken so that the hollow fiber membrane might not be stretched as much as possible. A bundle of the obtained hollow fiber membranes was inserted into a case, each of the ends of the bundle was attached and fixed with use of a polyurethane resin, and the resin was partially cut, to prepare a module with the ends of each of the hollow fiber membranes opened. The evaluation results were listed in Tables 1 and 2.

Example 2

Hollow fiber membranes were manufactured in the same manner as in Example 1 except that the drawing velocity from the coagulation liquid was set to 55.0 m/min., and a module was prepared.

Example 3

Hollow fiber membranes were manufactured in the same manner as in Example 1 except that the drawing velocity from the coagulation liquid was set to 59.0 m/min., and a module was prepared.

Example 4

Hollow fiber membranes were manufactured in the same manner as in Example 1 except that the discharge amount of the core solution was set to 2.08 cc/min., and a module was prepared.

Example 5

Hollow fiber membranes were manufactured in the same manner as in Example 1 except that the discharge amount of the core solution was set to 2.30 cc/min., and a module was prepared.

Example 6

Hollow fiber membranes were manufactured in the same manner as in Example 1 except that the discharge amount of the spinning dope was set to 1.88 cc/min., and a module was prepared.

Example 7

Hollow fiber membranes were manufactured in the same manner as in Example 1 except that the discharge amount of the spinning dope was set to 1.70 cc/min., and a module was prepared.

Comparative Example 1

Hollow fiber membranes were manufactured in the same manner as in Example 1 except that the discharge amount of the core solution was set to 2.40 cc/min., and a module was prepared.

Comparative Example 2

Hollow fiber membranes were manufactured in the same manner as in Example 1 except that the discharge amount of the core solution was set to 2.00 cc/min., and a module was prepared.

Comparative Example 3

Hollow fiber membranes were manufactured in the same manner as in Comparative Example 1 except that the drawing velocity from the coagulation liquid was set to 62.0 m/min., and a module was prepared.

Comparative Example 4

Hollow fiber membranes were manufactured in the same manner as in Comparative Example 2 except that the drawing velocity from the coagulation liquid was set to 53.0 m/min., and a module was prepared.

Comparative Example 5

19.0% by mass of cellulose triacetate, 68.85% by mass of NMP, and 12.15% by mass of TEG were uniformly dissolved to prepare a spinning dope. The obtained spinning dope was discharged from a slit portion of a double-tube nozzle together with water deaerated in advance and serving as a core solution at the same time, passed through an areal traveling portion shut out of external air by a spinning tube, was then introduced into a coagulation liquid having a temperature of 44° C. and having a ratio of NMP/TEG/water=59.5/10.5/30, and was coagulated. Subsequently, the hollow fiber membrane was subject to a washing process at 95° C. for 10 seconds with 5% stretching, subject to an 88% by mass glycerol bath at 95° C. for 3 seconds with 3% stretching, and dried with a drier. A module was prepared in the same manner as in Example 1 with use of the obtained hollow fiber membranes.

TABLE 1

| | Double-tube nozzle | | | | | Coagulation bath | |
|---|---|---|---|---|---|---|---|
| | Slit outside diameter (cm) | Slit inside diameter (cm) | Discharge amount of spinning dope (cc/min) | Discharge amount of core solution (cc/min) | Linear velocity ratio | Drawing velocity (m/min) | Draft ratio |
| Example 1 | 0.027 | 0.02 | 1.80 | 2.18 | 1.00 | 57.0 | 0.82 |
| Example 2 | 0.027 | 0.02 | 1.80 | 2.18 | 1.00 | 55.0 | 0.79 |
| Example 3 | 0.027 | 0.02 | 1.80 | 2.18 | 1.00 | 59.0 | 0.85 |
| Example 4 | 0.027 | 0.02 | 1.80 | 2.08 | 1.05 | 57.0 | 0.82 |
| Example 5 | 0.027 | 0.02 | 1.80 | 2.30 | 0.95 | 57.0 | 0.82 |
| Example 6 | 0.027 | 0.02 | 1.88 | 2.18 | 1.05 | 57.0 | 0.78 |
| Example 7 | 0.027 | 0.02 | 1.70 | 2.18 | 0.95 | 57.0 | 0.87 |
| Comparative Example 1 | 0.027 | 0.02 | 1.80 | 2.40 | 0.91 | 57.0 | 0.82 |
| Comparative Example 2 | 0.027 | 0.02 | 1.80 | 2.00 | 1.09 | 57.0 | 0.82 |
| Comparative Example 3 | 0.027 | 0.02 | 1.80 | 2.40 | 0.91 | 62.0 | 0.89 |
| Comparative Example 4 | 0.027 | 0.02 | 1.80 | 2.00 | 1.09 | 53.0 | 0.76 |
| Comparative Example 5 | 0.027 | 0.02 | 1.80 | 2.18 | 1.00 | 57.0 | 0.82 |

TABLE 2

| | Hollow fiber membrane | | | Recess | | | | Protein | | Strength and elongation | |
|---|---|---|---|---|---|---|---|---|---|---|---|
| | Outside diameter (μm) | Inside diameter (μm) | Membrane thickness (μm) | Long diameter (nm) | Short diameter (nm) | Aspect ratio | Depth (nm) | adsorption amount (mg/m²) | Δ TMP | Yield strength (g) | Breaking elongation (%) |
| Example 1 | 251 | 201 | 25 | 332 | 56 | 6 | 21 | 2.8 | 4.5 | 36 | 15 |
| Example 2 | 250 | 200 | 25 | 154 | 19 | 8 | 22 | 2.3 | 3.9 | 36 | 15 |
| Example 3 | 251 | 199 | 26 | 489 | 17 | 29 | 25 | 2.8 | 9.4 | 36 | 16 |
| Example 4 | 250 | 200 | 25 | 373 | 95 | 4 | 19 | 3.7 | 5.5 | 37 | 15 |
| Example 5 | 251 | 201 | 25 | 311 | 25 | 12 | 25 | 1.9 | 3.3 | 36 | 17 |

TABLE 2-continued

|  | Hollow fiber membrane | | | Recess | | | | Protein | | Strength and elongation | |
| --- | --- | --- | --- | --- | --- | --- | --- | --- | --- | --- | --- |
|  | Outside diameter (μm) | Inside diameter (μm) | Membrane thickness (μm) | Long diameter (nm) | Short diameter (nm) | Aspect ratio | Depth (nm) | adsorption amount (mg/m²) | Δ TMP | Yield strength (g) | Breaking elongation (%) |
| Example 6 | 252 | 200 | 26 | 333 | 18 | 19 | 28 | 1.8 | 3.5 | 35 | 16 |
| Example 7 | 246 | 200 | 23 | 305 | 13 | 23 | 17 | 2.1 | 5.5 | 37 | 15 |
| Comparative Example 1 | 252 | 200 | 26 | 356 | 11 | 32 | 25 | 3.7 | 15.0 | 34 | 12 |
| Comparative Example 2 | 251 | 201 | 25 | 366 | 148 | 2 | 47 | 5.1 | 6.3 | 34 | 13 |
| Comparative Example 3 | 250 | 200 | 25 | 535 | 16 | 33 | 7 | 4.2 | 18.6 | 37 | 14 |
| Comparative Example 4 | 250 | 200 | 25 | 270 | 133 | 2 | 61 | 6.0 | 6.8 | 35 | 13 |
| Comparative Example 5 | 246 | 200 | 23 | 432 | 12 | 36 | 66 | 9.4 | 33.7 | 33 | 22 |

As is apparent from Table 2, since each of the hollow fiber membranes in Examples 1 to 7 not only has a restricted amount of protein adsorbed on the inner surface thereof but also is excellent in filtration stability (low αTMP), blood purification can be conducted with high efficiency not only in normal hemodialysis but also in highly-loaded postdilution hemodiafiltration conditions. Conversely, since each of the hollow fiber membranes in Comparative Examples 1 and 3 has a high aspect ratio of the inner surface thereof, filtration stability is low, and the hollow fiber membrane is not suitable for hemodiafiltration. Also, each of the hollow fiber membranes in Comparative Examples 2 and 4 has a low aspect ratio of the inner surface thereof and thus has a problem of a large amount of adsorbed protein. Further, in the hollow fiber membrane in Comparative Example 5, not only the aspect ratio of the inner surface thereof is high, but also balance between yield strength and breaking elongation is out of a favorable range. The reason for this may be that stretching is significant in the washing processing and the glycerol dipping process. For this reason, the protein adsorption amount to the surface of the membrane is large, and the filtration stability is low.

INDUSTRIAL APPLICABILITY

A hollow fiber membrane according to the present invention has an asymmetric membrane structure containing a cellulose acetate-based polymer and including a dense layer at least on an inner surface side thereof and has high water permeability, molecular cutoff characteristics, and solute permeability. In particular, by optimizing the structure of the dense layer on the inner surface of the hollow fiber membrane, it is possible to provide a hollow fiber membrane having improved biocompatibility and having improved performance stability even under severe hemodiafiltration conditions to a patient with large body frame.

The invention claimed is:

1. A hollow fiber membrane comprising a dense layer at least on an inner surface side of the hollow fiber membrane, wherein
   when the inner surface of the hollow fiber membrane is observed under an atomic force microscope, a plurality of groove-like recesses oriented in a lengthwise direction of the hollow fiber membrane are observed,
   an aspect ratio defined as a ratio of a length to a width of each of the recesses is greater than or equal to 3 and less than or equal to 30,
   a yield strength of the hollow fiber membrane in a dry state is greater than 30 g/filament, and
   a breaking elongation is less than or equal to 20%/filament.

2. The hollow fiber membrane according to claim 1, wherein the hollow fiber membrane includes the dense layer and a support layer, and the support layer has a pore larger than a pore in the dense layer.

3. The hollow fiber membrane according to claim 1, wherein the hollow fiber membrane comprises a cellulose acetate-based polymer.

4. A hollow fiber membrane module comprising the hollow fiber membrane according to claim 1.

* * * * *